United States Patent [19]

Szabo et al.

[11] Patent Number: 4,569,926
[45] Date of Patent: Feb. 11, 1986

[54] STIMULATION OF PHAGOCYTOSIS WITH SOMATOSTATIN

[75] Inventors: Sandor Szabo, Brookline, Mass.; Klaus H. Usadel, Frankfurt, Fed. Rep. of Germany

[73] Assignee: Brigham and Women's Hospital, Boston, Mass.

[21] Appl. No.: 550,976

[22] Filed: Nov. 14, 1983

[51] Int. Cl.[4] .................. A61K 37/02; C07C 103/52
[52] U.S. Cl. .................................... 514/14; 514/806; 260/112.5 S
[58] Field of Search ................ 424/177; 514/14, 806; 260/112.5 S

[56] References Cited

U.S. PATENT DOCUMENTS 4,366,148 12/1982 Szabo et al. ................ 260/112.5 S

OTHER PUBLICATIONS

Chem. Abstracts vol. 92, 1980, 91960b, citation of Schusdziarra et al., *Science* 1980, 207(4430) 530-2.
Cornell et al., "Modulation of Hepatic...", J. Reticuloendothel. Soc. 1982; cited in Chem Abstracts, vol. 98, 1983, 83922z.

*Primary Examiner*—Nicky Chan
*Assistant Examiner*—Jacqueline M. Stone
*Attorney, Agent, or Firm*—Oblon, Fisher, Spivak, McClelland & Maier

[57] ABSTRACT

A method of increasing the clearance of particles from the blood stream of a vertebrate, which comprises administering to a vertebrate having a surplus of particles in the blood stream of the vertebrate an amount of somatostatin sufficient to increase phagocytosis in the vertebrate, is disclosed.

6 Claims, 3 Drawing Figures

STIMULATION OF PHAGOCYTOSIS WITH SOMATOSTATIN

BACKGROUND OF THE INVENTION

1. Field of the Invention

This invention relates to a method for stimulating phagocytes, particularly Kuppfer cells, in order to promote rapid clearing of particles, such as bacteria, viruses, and immune complexes from the blood stream of a vertebrate organism.

2. Description of the Prior Art

Somatostatin is a peptide hormone originally investigated because of its inhibitory effects against pituitary growth hormone, which is also known as somatotropin. Somatostatin is therefore sometimes known as somatotropin release inhibiting factor (SRIF). More recent studies have shown that pretreatment with exogenous somatostatin prevents cysteamine-induced duodenal ulcer, with minimal inhibition of gastric acid output (Schwedes et al, *Eur. J. Pharm.*, 44, 195 (1977)). In addition, somatostatin has been shown to have a beneficial effect on experimentally induced pancreatitis (Schwedes et al, *Horm. Metab. Res.*, 11, 142 (1979)), and adrenal and lung lesions (Schwedes et al, *Metabolism Suppl.*, 1, 27, 1377 (1978)). Thus, somatostatin has been demonstrated to be useful in the protection of various tissues against damage.

However, the objects of the present invention, as will hereafter be disclosed, are not primarily to prevent damage to tissues but to increase the activity of certain cells, an activity of somatostatin not previously disclosed in the prior art.

SUMMARY OF THE INVENTION

Accordingly, it is an object of this invention to provide a method of stimulating phagocytosis in a vertebrate.

It is a further object of this invention to provide a method of stimulating phagocytosis in a vertebrate having a surplus of particles in the blood of said vertebrate.

It is yet another object of this invention to provide a method of protecting a vertebrate against bacterial and viral infections by increasing the clearing rate of particles by Kuppfer cells and macrophages.

It is a still further object of this invention to provide a method of removing immune complexes, therapeutic and diagnostic compositions, synthetic toxins, and endotoxins from the blood stream of a vertebrate.

These and other objects of the invention as will hereinafter become more readily apparent have been accomplished by providing a method of increasing phagocytosis in a vertebrate having a surplus of particles in the blood stream of said vertebrate, which comprises administering to said vertebrate an amount of somatostatin effective to increase the activity of phagocytes in said vertebrate in clearing said particles from said blood stream.

BRIEF DESCRIPTION OF THE DRAWINGS

A more complete appreciation of the invention and many of the attendant advantages thereof will be readily obtained by reference to the following detailed description when considered in connection with the accompany drawings, wherein.

DESCRIPTION OF THE PREFERRED EMBODIMENTS

Figure 1:
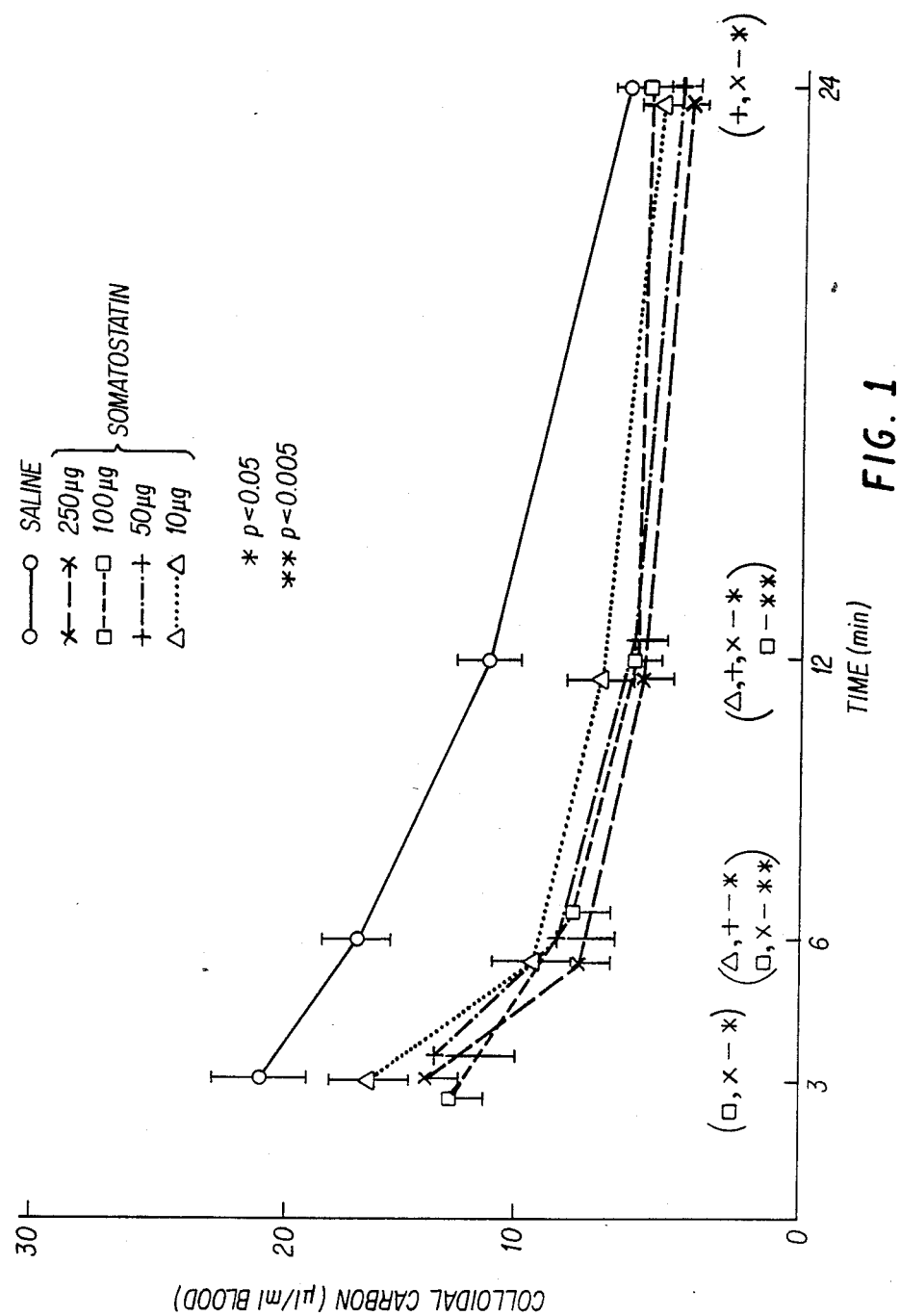
FIG. 1 is a graph showing the dose-dependent effect of somatostatin on colloidal carbon clearance from the blood of a rat.

The structure of somatostatin has been established by analytical investigations and chemical synthesis. Somatostatin is a cyclic tetradecapeptide having the following structure:

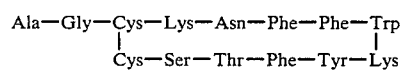

Somatostatin can be isolated from bovine hypothalamic extracts, as disclosed in Brazeau et al, *Science*, 179, 77 (1973) or can be synthesized, for example, as disclosed in Rivier et al, *Compt. Rend., Ser. D*, 276, 2737 (1973); Sarantakis et al, *Biochem. Biophys. Res. Commun.*, 54, 234 (1973); Yamashiro et al, ibid, 882; and Coy et al, ibid, 1267, all of which disclosures of isolation and syntheses being hereby incorporated by reference. The synthetic linear form of the peptide shows identical biological activity to the natural cyclic or synthetic cyclic (oxidized) forms, all of which are considered to be encompassed by the single term "somatostatin" for the purposes of this invention.

Various previous studies have shown that somatostatin is effective for preventing deterioration of various animal tissues, such as the articles discussed in the prior art section of this application. The prior patent of the present inventors, U.S. Pat. No. 4,366,148, discloses that somatostatin is effective for preventing lesions of blood vessels, especially lesions of hepatic blood vessels in mammals. Applicants have now discovered that somatostatin has an additional effect in that it is also effective in increasing the activity of phagocytes in vertebrates. Thus, the present invention encompasses a new activity of somatostatin and its analogues which was not taught by the prior art. Somatostatin is administered to a vertebrate having a surplus of particles in the blood stream of said vertebrate, in an amount effective to increase the rate of phagocytosis in said vertebrate. Thus, somatostatin leads to more rapid clearing of particles from the blood stream of vertebrates when administered in accordance with the present invention than would occur in the absence of the administered somatostatin.

By "particles" is meant substances in the colloidal particle size range as commonly understood. Typical colloidal particles have an average diameter in the range from 10 to 300 μm. However, since phagocytes recognize and avoid naturally occurring particles present in the bloodstream, such as red blood cells, such materials will not be removed when phagocytosis is stimulated in accordance with this invention. Thus, as used herein, "particle" does not encompass blood cells or other natural molecules, complexes, or cells that are present in amounts normally found in the vertebrate and which are not normally engulfed by phagocytes. However, immune complexes, such as would be present either in an infection (e.g., by bacteria) or an autoimmune disease, are considered to be within the scope of the term "particles". The same is true of damaged or modified cells or other substances which are normally removed by phagocytes.

The present invention is intended principally to aid in the clearing of viruses, bacteria, and immune complexes from the blood stream of vertebrates. However, the invention may also be carried out on a vertebrate which was previously injected with a diagnostic or therapeutic agent in order to reduce the amount of agent present in the blood stream. For example, liposomes are often used as carriers of therapeutic agents and would be removed by the stimulated phagocytosis of the present invention. Other examples of colloidal particles against which the present invention can be used include endotoxins and synthetic toxins.

The structure of somatostatin has been disclosed above. Derivatives and analogues of somatostatin having similar structure (such as those in which free carboxylates are esterified or free amino groups are acetylated) and biological effects are considered to be encompassed by this invention. Both cyclic and linear derivatives are permissible. Preferred is somatostatin itself, either in linear or cyclic form. Some somatostatin analogues having greatly different structure and their uses are discussed, and methods of using such compounds are claimed, in an application by Szabo, Usadel, and Kessler filed on even date with this application.

Somatostatin may be used to treat any vertebrate having functioning phagocytes in its blood stream or organs (especially any mammal), although treatment of humans is preferred. Suitable dosages of somatostatin are 1 μg to 10 mg/kg of body weight, preferably 0.02 to 1.5 mg/kg, and more preferably 0.06 to 1.0 mg/kg. Administration may be in a single dose or may be spread out over time by administration of multiple small doses or by slow continuous intravenous administration of a dilute solution of somatostatin. The maximum dose per day should not exceed 10 mg/kg of body weight.

The dosage may be administered by intravenous, subcutaneous or intramuscular injection or intragastrically. Inhalation or rectal administration is also suitable. Administration by intravenous or subcutaneous injection is preferred. When administered in the form of an injection, any non-toxic pharmaceutical carrier may be used, provided that the carrier does not cause hydrolysis of the somatostain peptide bonds or otherwise interfere with the action of somatostatin. Suitable carriers include water, aqueous solutions of non-toxic salts and organic compounds, and non-toxic organic solvents, such as ethanol. Preferred are isotonic aqueous solutions, such as solution of NaCl and glucose. Most preferred for subcutaneous injections are solutions containing protamine sulfate and $ZnCl_2$ (about 0.05% and about 0.13 mg/ml, respectively) as these materials prolong the activity of somatostatin, particularly when injected subcutaneously.

Somatostatin may be administered alone or concurrently with other medicinal materials. Preferred is administration with other materials that also alleviate the condition being treated, for example, antibiotics or immune response stimulants, such as interferon.

Administration may occur after the presence of an infection is suspected or confirmed, or under conditions in which surplus particles would be expected to be present, for example, after administration of radioactive liposomes in a diagnostic technique.

The effectiveness of somatostatin and its analogues in increasing phagocytosis has been demonstrated in a model study using carbon particles. Rats were injected either with saline or with a colloidal carbon suspension, and the time required for clearing of colloidal particles from the blood stream was measured. In a comparative experiment, zymosan, an agent known to increase the activity of phagocytes, was administered instead of the somatostatin analogue. In rats which received injections of saline, the disappearance of colloidal carbon from the blood was virtually linear, an expected result based on previous studies by others. Administration of somatostatin markedly accelerated the carbon clearance. Phagocytosis of carbon particles was particularly enhanced for Kuppfer cells, the fixed histiocytes present on the walls of the liver sinusoids, and other macrophages in the liver, lung and spleen. Somatostatins were demonstrated by these studies to be more effective than zymosan in stimulating clearing potency.

The above disclosure generally describes the present invention. A more complete understanding can be obtained by reference to the following specific examples, which are provided herein for purposes of illustration only and are not intended to be limiting unless otherwise specified.

EXAMPLE

Figure 2:
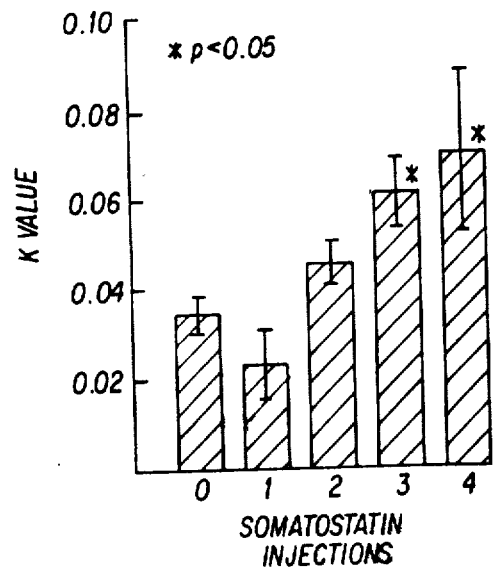
FIG. 2 is a graph showing time-dependent action of somatostatin on colloidal carbon clearance from the blood of a rat.
Figure 3:
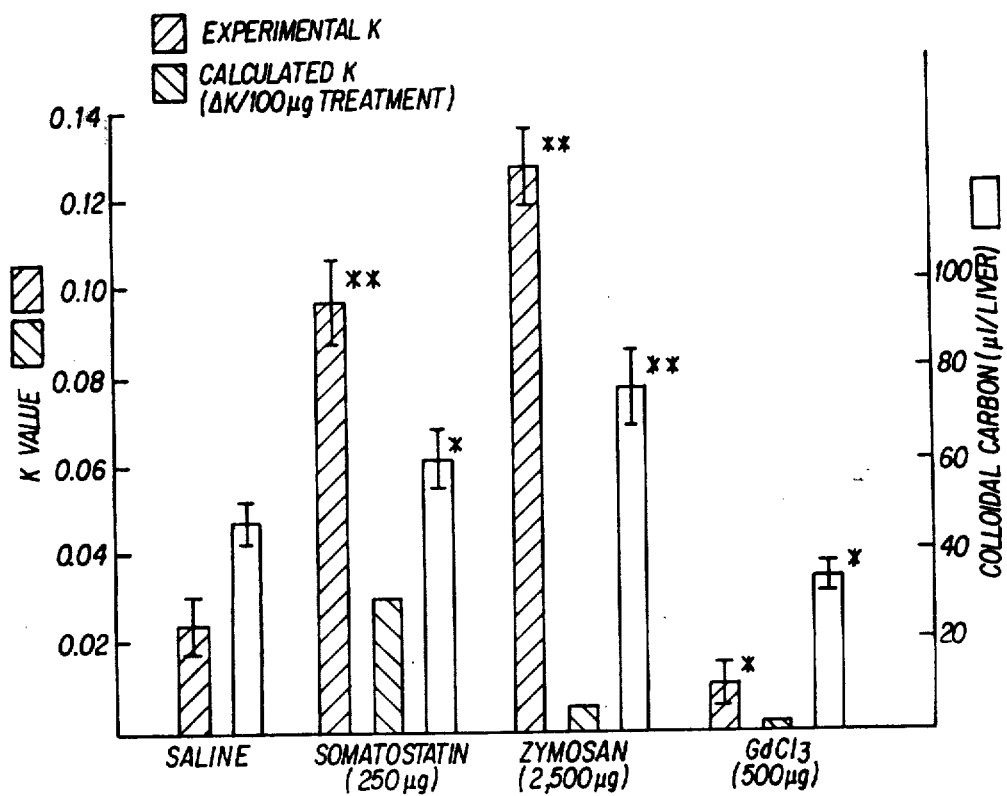
FIG. 3 is a graph showing the effect of somatostatin, zymosan, and gadolinium chloride on colloidal carbon clearance from the blood and hepatic uptake of carbon in a rat.

All of the experiments were performed in female Spraque-Dawley rats (ESS Laboratories, Lynnfield, Mass.) with an initial body weight of 150-180 g, and with unlimited access to Purina laboratory chow and tap water. Control and experimental groups consisted of 3-4 rats. Each experiment was repeated at least twice and the results were pooled. Linear or cyclic somatostatin (Serono) was injected under mild ether anesthesia at 10, 50, 100 or 250 μg in 0.5 ml of saline into the jugular vein once daily for 4 consecutive days in the dose-response study (FIG. 1). Control animals were injected with the same amount of saline. In the time-response study, 0, 1, 2, 3 or 4 daily doses of somatostatin, 50 μg, were injected i.v. (FIG. 2). In the comparative experiments, somatostatin, 250 μg, i.v., was given as in the first study, and standard doses of zymosan (Sigma 2,500 μg/100 g i.v.; twice, 48 and 24 hr before colloidal carbon) and the reticuloendothelial system (RES) blocker gadolinium chloride (Sigma; 500 μg/100 g i.v.; once, 24 hour prior to india ink) were administered to additional groups of rats (FIG. 3). In all of the experiments, 0.1 ml/100 g of the supernatant of centrifuged (3000 rpm/15 min) colloidal carbon (Wagner's india ink) was injected i.v. under mild ether anesthesia. Blood samples (50 μl) were obtained with heparinized glass capillaries and by puncture of the retro-orbital venous plexus at 3, 6, 12 and 24 minutes after the administration of carbon. The blood samples were lysed in 2 ml of 0.1% $Na_2CO_3$ solution. After 24 minutes, the rats were killed, and the livers were perfused through the portal vein with 20 ml saline to remove trapped blood. Samples of liver, spleen, lung and kidney were fixed in 10% formalin and subsequently processed for light microscopy. A piece of liver was digested in concentrated mineral acid, and, following organic extraction, the concentration of carbon, as in blood hemolysates, was measured spectrophotometrically at 660 nm using the method of Takahashi and Matsuoka (*J. Toxicol. Sci., S.*, 1 (1980).

The phagocytic index or K value was calculated as described by others (Takahashi and Matsuoka, ibid; Biozzi et al, *J. Exp. Pathol.*, 34, 441 (1953)) to indicate the carbon clearance for the blood. Since it was evident that the effect of treatment was maximal on carbon clearance during the first 6 or 12 minutes, K values were obtained only for this time interval. For statistical evaluation, Student's two-tailed t-test was used.

In rats which received daily injections of saline (0.5 ml), i.v., the disappearance of colloidal carbon from the blood was virtually linear (FIG. 1) and identical to absolute control rats in other experiments (not shown). Administration of somatostatin markedly accelerated the carbon clearance; this effect was most dramatic during the first 6–12 minutes (FIG. 1). Doses of 50, 100 or 250 $\mu$g of somatostatin produced very similar results, only 10 $\mu$g was less effective than the other doses (FIG. 1). These results still indicate that somatostatin in doses below 10 $\mu$g may accelerate carbon clearance. Considering the short half-life of the injected peptide, this indicates a high potency of action in stimulating Kupffer cells and RES. On the other hand, multiple injections of somatostatin are needed for RES stimulation, since only three or four doses (one per day) resulted in significantly enhanced phagocytic index of K value (FIG. 2).

The efficacy of somatostatin was also compared with that of other agents known to affect RES function. Zymosan in standard doses (i.e., about 10 times higher than that of somatostatin) indeed stimulated carbon clearance from the blood and uptake of the carbon to the liver, similarly to the action of the peptide, while $GdCl_3$ inhibited these parameters (FIG. 3). Unfortunately, since the molecular weight of zymosan is not known, molar comparisons of these actions are impossible. A crude comparison was obtained by calculating the change in K caused by 100 $\mu$g of treatment ($\Delta$K/100 $\mu$g), thus demonstrating a clearing potency of the following order: somatostatin > zymosan > $GdCl_3$.

Light microscopic examination of liver sections revealed easily detectable black carbon particles in Kupffer cells, especially in the periportal areas, where the majority of these phagocytic cells are known to be located. This differential distribution of carbon-deposition was especially prominent in the liver of those rats which had been given somatostatin which caused numerous macrophages to take up carbons.

The invention now being fully described, it will be apparent to one of ordinary skill in the art that many changes and modifications can be made thereto without departing from the spirit or scope of the invention as set forth herein.

What is claimed as new and desired to be claimed by letters patent of the United States is:

1. A method of increasing the phagocytosis of exogeneous colloidal particles from blood, which comprises:
   injecting into a mammal having a greater than normal amount of exogeneous colloidal particles in the blood stream of said mammal and a need for the removal of said particles an amount of somatostatin sufficient to increase the activity of phagocytes in said mammal.

2. The method of claim 1, wherein somatostatin is administered in an amount of from 0.02 to 1.5 mg/kg of body weight.

3. The method of claim 2, wherein said amount is from about 0.06 to about 1.0 mg/kg of body weight.

4. The method of claim 1, wherein said injecting is by intravenous or subcutaneous injection.

5. The method of claim 1, wherein said injecting is to a human.

6. A method of increasing the phagocytosis of exogeneous colloidal particles from blood, which comprises:
   administering to a mammal having a greater than normal amount of exogeneous colloidal particles in the blood stream of said mammal and a need for the removal of said particles an amount of somatostatin sufficient to increase the activity of phagocytes in said mammal, wherein said administering is by intragastric, inhalation, or rectal administration.

* * * * *

UNITED STATES PATENT AND TRADEMARK OFFICE
CERTIFICATE OF CORRECTION

PATENT NO. : 4,569,926

DATED : February 11, 1986

INVENTOR(S) : Sandor Szabo et al.

It is certified that error appears in the above-identified patent and that said Letters Patent is hereby corrected as shown below:

The sheet of drawing consisting of figures 2 and 3 should be added as per attached sheet.

Signed and Sealed this

Eighth Day of July 1986

[SEAL]

Attest:

Attesting Officer

DONALD J. QUIGG

Commissioner of Patents and Trademarks